United States Patent
Lin et al.

(10) Patent No.: US 11,684,696 B2
(45) Date of Patent: Jun. 27, 2023

(54) PREPARATION METHOD OF GRADIENT MINERALIZED CANCELLOUS BONE MATRIX MATERIAL

(71) Applicants: SIR RUN RUN SHAW HOSPITAL ZHEJIANG UNIVERSITY SCHOOL OF MEDICINE, Zhejiang (CN); ZHEJIANG DISAI BIOTECHNOLOGY CO., LTD, Zhejiang (CN)

(72) Inventors: Xianfeng Lin, Zhejiang (CN); Shijie Liu, Zhejiang (CN); Yiyun Wang, Zhejiang (CN); Yazhi Lu, Zhejiang (CN); Shunwu Fan, Zhejiang (CN)

(73) Assignees: SIR RUN RUN SHAW HOSPITAL ZHEJIANG UNIVERSITY SCHOOL OF MEDICINE, Zhejiang (CN); ZHEJIANG DISAI BIOTECHNOLOGY CO., LTD, Zhejiang (CN)

( * ) Notice: Subject to any disclaimer, the term of this patent is extended or adjusted under 35 U.S.C. 154(b) by 456 days.

(21) Appl. No.: 17/040,999

(22) PCT Filed: Mar. 12, 2019

(86) PCT No.: PCT/CN2019/077754
§ 371 (c)(1),
(2) Date: Sep. 24, 2020

(87) PCT Pub. No.: WO2020/147181
PCT Pub. Date: Jul. 23, 2020

(65) Prior Publication Data
US 2021/0121605 A1 Apr. 29, 2021

(30) Foreign Application Priority Data
Jan. 17, 2019 (CN) .......................... 201910044252.7

(51) Int. Cl.
*A61L 27/54* (2006.01)
*A61L 27/36* (2006.01)

(52) U.S. Cl.
CPC ......... *A61L 27/3608* (2013.01); *A61L 27/365* (2013.01); *A61L 27/3633* (2013.01); *A61L 27/3687* (2013.01); *A61L 27/3691* (2013.01); *A61L 27/54* (2013.01); *A61L 2300/412* (2013.01); *A61L 2430/02* (2013.01); *A61L 2430/40* (2013.01)

(58) Field of Classification Search
None
See application file for complete search history.

(56) References Cited

FOREIGN PATENT DOCUMENTS

CN 106215238 A * 12/2016

OTHER PUBLICATIONS

CAS Common Chemistry—Triton X-100, as obtained from the Internet at https://commonchem-istry.cas.org/detail?cas_rn=9002-93-1 on Feb. 14, 2023. (Year: 2023).*

* cited by examiner

Primary Examiner — David J Blanchard
Assistant Examiner — Daniel F Coughlin

(57) ABSTRACT

A gradient mineralized cancellous bone matrix material and a preparation method thereof are provided, and the preparation method includes: processing naturally-derived bone tissue with an immunogenicity removal treatment for decellularization, and processing an obtained decellularzed bone with a gradient demineralization treatment to obtain the gradient mineralized cancellous bone matrix material. The present invention expands a porosity of the bone matrix material and a collagen exposure degree on a surface thereof, which effectively releases growth factors and improves adhesion of the material to the cells, so as to up-regulate genes and proteins related to cell regeneration. The present invention not only retains the biomechanical properties and three-dimensional microstructure of natural bone ECM scaffolds, but also plays an active role for osteogenesis, angiogenesis and collagen mineralization in the early stage of fracture, thereby increasing engraftment adhesion of cells and promoting differentiation induction of cells.

9 Claims, 9 Drawing Sheets

PREPARATION METHOD OF GRADIENT MINERALIZED CANCELLOUS BONE MATRIX MATERIAL

BACKGROUND OF THE PRESENT INVENTION

Field of Invention

The present invention relates to a technical field of bone tissue repair and regeneration, and more particularly to a natural-tissue-derived gradient mineralized cancellous bone matrix material and a preparation method thereof.

Description of Related Arts

Bone regeneration is a long process, and most of the serious bone defects are difficult to repair by themselves. Conventionally, bone graft materials have been considered as an alternative treatment than can be widely used. Among them, natural bone tissue, especially natural cancellous bone matrix, is rich in collagen, growth factors and other substances that promote cell growth and bone tissue repair. Furthermore, it also contains a lot of minerals (including $Ca^{2+}$, $PO4^{-3}$, $Mg^{2+}$ and other ions). In recent years, more and more studies have shown that mineral ions ($Ca^{2+}$, $PO4^{-3}$, $Mg^{2+}$, etc.) have extremely important regulating and promoting effects on the repair of new bone tissue, osteogenesis-related angiogenesis, collagen mineralization, etc. In addition, the mineral content also affects material properties such as three-dimensional structure, porosity and microscopic biomechanical. Characterization of the above materials has a significant regulatory effect on bone repair and regeneration. For example, studies have shown that the hardness and elastic modulus of the material can significantly promote osteoblast behavior induction and bone repair ability, and biological collagen mineralization is also believed by more and more scholars to significantly promote the osteogenesis and bone tissue regeneration process.

In recent years, biomaterials derived from natural bone matrix have been gradually prepared and initially used in clinic. However, due to lack of early research on the theoretical mechanism of bone repair, the conventional bone matrix materials have certain detects. For example, it was reported that cancellous bone ECM (Extracellular matrix) scaffold material was prepared by completely removing the cellular components of the natural bone matrix, thereby reducing immunogenicity and promoting bone repair. However, bone repair needs to go through a hematoma organizing period, a callus formation period and a callus shaping period, and the application of biological materials is commonly before and after the hematoma organizing period, so the mature, dense and fully-mineralized bone ECM material cannot be well fused with new bone to promote regeneration. There are also reports in the literature that fully demineralized bone matrix materials were used for bone tissue repair and regeneration. Conventional treatment process uses strong acid and long-term EDTA-2Na soaked decalcification, which often causes irreversible damage to the natural bone ECM scaffold material and leads to the decline of biomechanical properties, the loss of minerals and growth active factors, and the change of three-dimensional microstructure. As a result, biological regeneration repair activity of the scaffold is seriously decreased.

SUMMARY OF THE PRESENT INVENTION

For overcoming conventional technique defects, an object of the present invention is to provide a natural-tissue-derived gradient mineralized decellularized cancellous bone matrix material and a preparation method thereof.

The present invention provides a preparation method of a gradient mineralized cancellous bone matrix material, comprising: processing naturally-derived bone tissue with an immunogenicity removal treatment for decellularization, and processing an obtained decellularized bone with an ultrasound gradient demineralization treatment to obtain the gradient mineralized cancellous bone matrix material.

The preparation method comprises specific steps of:

Step 1: randomly selecting bone tissue from a mammal, removing the bone tissue with a drill, and cutting the bone tissue into cylindrical bone blocks with a scalpel;

Step 2: then rinsing the bone blocks with sterile physiological saline for 2 hours before sterilizing by irradiation, wherein an irradiation dose is 5-40 w;

Step 3: rinsing the bone blocks with deionized water containing protease inhibitor to remove blood, fat tissue and other impurities, wherein a concentration of the protease inhibitor in the deionized water is 10-50 KIU/ml, and the bone blocks are rinsed with the deionized water for 2-6 times and 3-20 minutes for each time;

Step 4: separating the bone blocks into an embedding box, and putting the embedding box into a deionized water solution containing acetone and shaking for 1-4 hours, wherein a volume ratio of the acetone to deionized water in the deionized water solution is 10%-20%;

Step 5: putting the embedding box into a deionized water solution containing tributyl phosphate and shaking for 1-4 hours, wherein a volume ratio of the tributyl phosphate to deionized water in the deionized water solution is 1%-5%;

Step 6: putting the embedding box in a deionized water solution containing the protease inhibitor, shaking at 4° C. for 24-48 hours with a shaker, and then freezing and thawing with liquid nitrogen for 2-6 cycles, wherein each cycle is from −80° C. to 37° C., and a shaker speed is 50-300 rpm;

Step 7: putting the embedding box in a buffer solution containing Triton® X-100, and shaking with a constant temperature shaker for 24 hours, wherein a concentration of the Triton® X-100 is 0.5-5%;

Step 8: shaking the embedding box in a buffer solution containing SDS with the constant temperature shaker for 36 h, wherein a concentration of the SDS is 0.5-10%;

Step 9: putting the embedding box in a PBS buffer solution having a concentration of potassium chloride of 0.1-1M, and shaking with the shaker at 4° C. and 100 rpm for 2-12 hours;

Step 10: shaking the embedding box in a PBS buffer containing potassium iodide with the shaker at 4° C. and 100 rpm for 2-12 hours, wherein a concentration of the potassium iodide in deionized water is 1-1.5M;

Step 11: performing the ultrasound gradient demineralization treatment in a NaOH buffer solution containing EDTA2Na at 4° C.-10° C. for 4, 8, 12 and 24 hours, so as to obtain bone ECM (Extracellular matrix) materials with mineralization degrees of 100%, 90%, 60% and 0%; and Step 12: sterilizing the obtained materials by irradiation; wherein after each of the Steps 4-11, the deionized water is used to rinse for 6 hours before a next step.

Preferably, in the deionized water containing the protease inhibitor, the concentration of the protease inhibitor is 20-40 KIU.

Preferably, in the deionized water solution containing the acetone, the volume ratio of the acetone to the deionized water is 13%-18%.

Preferably, in the deionized water solution containing the tributyl phosphate, the volume ratio of the tributyl phosphate to the deionized water is 2%-5%.

Preferably, the shaker speed is 30-180 rpm.

Preferably, the concentration of the Triton® X-100 is 0.5-3%

Preferably, the concentration of the SDS is 0.5-5%

Preferably, the concentration of the potassium chloride in deionized water is 0.3-1M.

Preferably, the concentration of the potassium iodide in the deionized water is 1-1.4M.

The present invention also provides a specific gradient mineralized cancellous bone ECM scaffold material.

Preferably, mineralization degrees of the gradient mineralized cancellous bone ECM scaffold material are 90% and 60%.

Preferably, a source of the material is porcine scapula.

Beneficial Effects of the Present Invention

The present invention adopts low temperature, precise and rapid supergene gradient demineralization treatment to prepare the natural-tissue-derived gradient mineralized cancellous bone matrix material with better regeneration and repair effect. Such material has low immunogenicity, rich biologically active components, good biomechanical properties, three-dimensional microstructure and a certain degree of mineral enrichment ($Ca^{2+}$, $PO4^{-3}$, etc.), which has a good promotion effect on excellent regeneration of new bone tissue and vascularization. It can be used to repair bone regeneration disorders such as bone defects and bone non-union caused by various clinical diseases. Moreover, the present invention can also provide a brand new precise gradient mineralized cancellous material system based on natural bone matrix for the research of biomineralization materials.

Compared with conventional non-demineralized or fully-demineralized natural bone matrix products, the present invention (bone ECM materials with the mineralization degrees of 90% and 60%) is significant in:

1) The specific low temperature and precise partial demineralization treatment expands a porosity of the bone matrix material and a collagen exposure degree on a surface thereof, which effectively releases growth factors and improves adhesion of the material to the cells, so as to up-regulate genes and proteins related to cell regeneration.

2) On the other hand, the certain degree of mineral enrichment ($Ca^{2+}$, $PO4^{-3}$, etc.) not only retains the biomechanical properties and three-dimensional microstructure of natural bone ECM scaffolds, but also plays an active role for osteogenesis, angiogenesis and collagen mineralization in the early stage of fracture (hematoma organizing stage), thereby increasing engraftment adhesion of cells and promoting differentiation induction of cells.

3) The natural-tissue-derived gradient mineralized cancellous (mineralization degrees of 90% and 60%) bone extracellular matrix materials have more potential than non-demineralized or fully-demineralized bone matrix materials in promoting mesenchymal stem cells differentiation and osteogenesis.

DETAILED DESCRIPTION OF THE PREFERRED EMBODIMENT

Figure 1A:
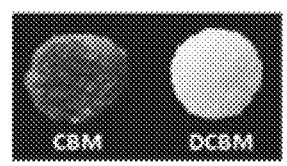
FIG. 1A and FIG. 1B are general appearance images of gradient mineralized decellularized cancellous bone matrix materials.

The present invention provides a natural-tissue-derived gradient mineralized cancellous bone matrix material and a preparation method thereof.

Figure 1B:
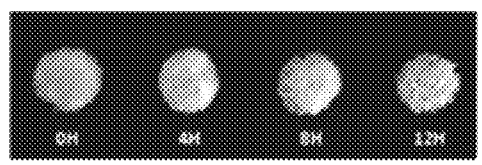

Embodiment 1: Preparation of Porcine Scapula Specifically Demineralized Cancellous Bone ECM Material 1) selecting fresh porcine scapula and washing for 4 times with sterile saline, removing cancellous bone with a 6 mm drill, and cutting the cancellous bone into cylindrical bone blocks about 2 mm high with a scalpel;

2) then rinsing the bone blocks with sterile physiological saline for 2 hours before sending to an irradiation center for sterilizing by irradiation, wherein an irradiation dose is 25 w:

3) rinsing the bone blocks with deionized water containing 20 KIU/ml protease inhibitor for 3 times and 10 minutes for each time, to remove blood, fat tissue and other impurities;

4) preparing high-temperature sterilized 1 L glass bottles containing 500 ml deionized water and preparing 20 embedding boxes on a sterile operating table with sterile gloves; separating 3 sterilized bone blocks into each embedding box, and putting the embedding box into 10 ml deionized water solution containing 15% acetone and shaking at 10° C. for 2 hours;

5) putting the embedding box into 5 ml deionized water solution containing 2% tributyl phosphate and shaking at 10° C. for 4 hours;

6) putting the embedding box in a deionized water solution containing the protease inhibitor, shaking at 4° C. and 50 rpm for 24 hours with a shaker, and then freezing and thawing with liquid nitrogen for 3 cycles (−80° C./37° C.);

7) putting the embedding box in 5 ml 2% Triton® X-100, and shaking with a constant temperature shaker at 10° C. and 100 rpm for 24 hours;

8) shaking the embedding box in deionized water containing 5% SDS with the constant temperature shaker at 10° C. and 100 rpm for 36 h;

9) putting the embedding box in a PBS buffer solution containing 0.5M potassium chloride, and shaking with the shaker at 4° C. and 100 rpm for 6 hours;

10) shaking the embedding box in a PBS buffer containing 1M potassium iodide with the shaker at 4° C. and 100 rpm for 6 hours, to obtain decellularized bone ECM materials (as shown in FIG. 1A);

11) preparing a decalcification solution (deionized water 1750 ml EDTA-2Na 450 g NaOH 35 g); taking out the bone blocks and decalcifying in an ultrasound decalcifier at 250 kHz and 4° C. for 4, 8, 12 and 24 h;

12) after each of the steps 4)-11), rinsing with the deionized water for 6 hours before a next step; and 13) taking out the bone blocks to obtain bone ECM materials with mineralization degrees of 100%, 90%, 60% and 0% (as shown in FIG. 1B), and sterilizing the obtained materials by 25 w irradiation.

Embodiment 2: Detection of Porcine Scapula Bone ECM Material With Mineralization Degrees of 90% and 60%

Figure 1C:
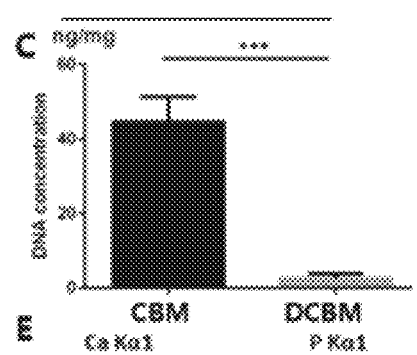
FIG. 1C is a histogram illustrating that DNA content of the decellularized material is significantly reduced, and almost contains no cellular components and immunogenic substances.
Figure 1D:
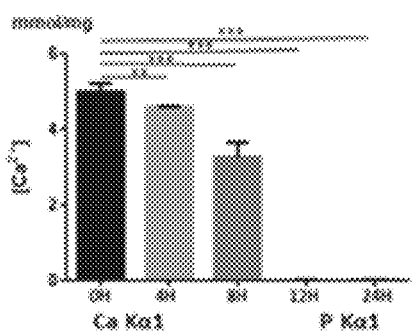
FIG. 1D is a histogram illustrating materials with mineralization degrees of 100%, 90%, 60% and 0% after gradient demineralization.
Figure 3A:
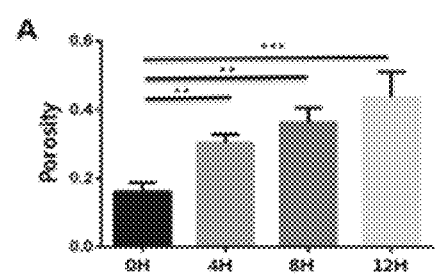
FIG. 3A and FIG. 3B are histograms indicating that porosity of the demineralized bone ECM material is increased, and stiffness of deformation resistance index is decreased.
Figure 3B:
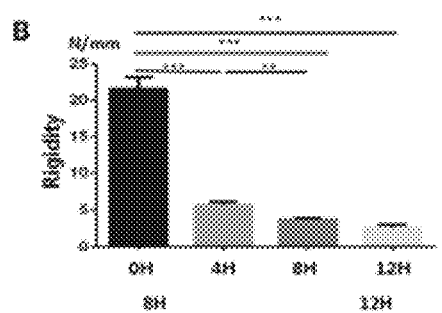

1)-2) are the same as those of the embodiment 1;

3) rinsing the bone blocks with deionized water containing 10 KIU/ml protease inhibitor for 3 times and 20 minutes for each time, to remove blood, fat tissue and other impurities;

4) preparing high-temperature sterilized 1 L glass bottles containing 500 ml deionized water and preparing 20 embedding boxes on a sterile operating table with sterile gloves; separating 3 sterilized bone blocks into each embedding box, and putting the embedding box into 10 ml deionized water solution containing 15% acetone and shaking at 10° C. for 4 hours;

5)-13) are the same as those of the embodiment 1;

14) detecting DNA contents in the decellularized materials, which are very a shown in FIG. 1C);

15) detecting mineralization contents the bone ECM materials with the mineralization degrees of 100%, 90%, 60% and 0% (taking calcium ion contents as an example), wherein the bone ECM material group with the mineralization degree of 90% (4 h demineralization) is 4.58±0.01 mmol/mg, the bone ECM material group with the mineralization degree of 60% (8 h demineralization) is 3.26±0.38 mmol/mg, the bone ECM material with the mineralization degree of 0% (12 h demineralization) contains almost no calcium ion; (the bone ECM material with the mineralization degree of 100% (non-demineralized material) has a calcium ion content of 4.99±0.22 mmol/mg) (as shown in FIG. 1D);

16) detecting porosities of the bone ECM materials with the mineralization degrees of 100%, 90%, 60% and 0%, wherein the porosity increases with the demineralization time (as shown in FIG. 3A); and 17) detecting stiffnesses of the bone ECM materials with the mineralization degrees of 100%, 90%, 60% and 0%, wherein the stiffness is an indicator of resistance to stress and deformation; as the mineralization degree decreases, the stiffness of corresponding material also decreases in sequence; the stiffnesses of the bone ECM materials with the mineralization degrees of 100%, 90%, 60% and 0% (4 h, 8 h and 12 h demineralization) are 5.71±0.46N/mm, 3.68±0.18N/mm, and 2.53±1.62N/mm (the stiffness of the hone ECM material with the mineralization degree of 100% (non-demineralized material) is 21.55±1.62N/mm) (as shown in FIG. 3B).

Embodiment 3: Characterization of Porcine Scapula Bone ECM Material With Mineralization Degrees of 90% and 60%

Figure 2A:
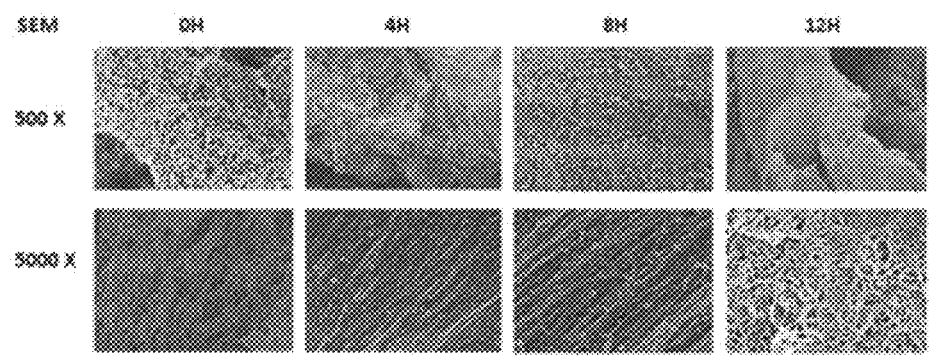
FIG. 2A is scanning electron micrographs indicating that under 500 times magnification observation, surfaces of a demineralized bone ECM material are smoother and calcium nodule distribution is reduced, and under 5000 times magnification observation, exposure of mineralized collagen fiber is increased after the mineralization degree of the material is reduced.
Figure 3C:
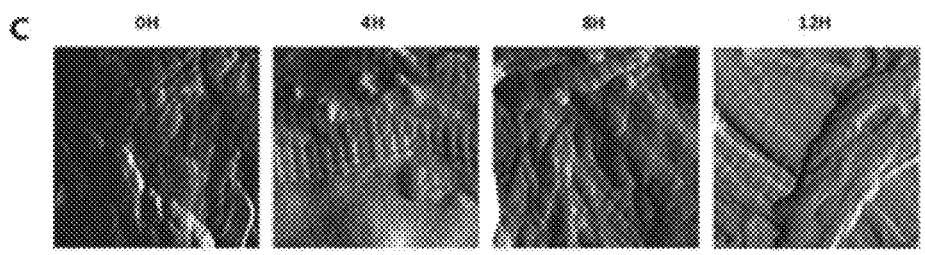
FIG. 3C is images indicating frontal force difference of the bone ECM materials with different mineralization degrees (scale bar of 1 μm)
Figure 3D:
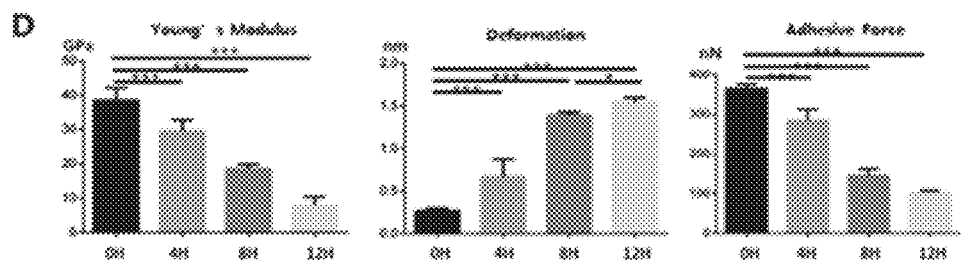
FIG. 3D is histograms of micromechanics property changes of the hone ECM material, wherein as the mineralization degree is decreased, Young's modulus on material surfaces is decreased, deformation is increased, and adhesion force is decreased.

1)-2) are the same as those of embodiment 1;

3) rinsing the bone blocks with deionized water containing 50 KIU/ml protease inhibitor for 2 times and 10 minutes for each time, to remove blood, fat tissue and other impurities;

4) preparing high-temperature sterilized 1 L glass bottles containing 500 ml deionized water and preparing 20 embedding boxes on a sterile operating table with sterile gloves; separating 3 sterilized bone blocks into each embedding box, and putting the embedding box into 10 ml deionized water solution containing 10% acetone and shaking at 10° C. for 1 hours;

5) putting the embedding box into 5 ml deionized water solution containing 5% tributyl phosphate and shaking at 10° C. for 3 hours;

6) putting the embedding box in a deionized water solution containing the protease inhibitor, shaking at 4° C. and 50 rpm for 36 hours with a shaker, and then freezing and thawing with liquid nitrogen for 2 cycles (−80° C./37° C.);

7)-13) are the same as those of embodiment 1;

14) observing with a scanning electron microscopy (SEM) to obtain ultrastructural characteristics of the bone ECM materials with the mineralization degrees of 100%, 90%, 60% and 0%, wherein compared with the other groups, the bone ECM materials with the mineralization degrees of 100% and 90% (0 and 4 h demineralization) have rougher surfaces and smaller pores; in addition, structures and arrangement of collagen fibers are also different among the four groups; in the bone ECM material group with the mineralization degree of 100% (non-demineralized material), most of the collagen fibers are covered by the surface, while on the surfaces of the bone ECM materials with the mineralization degrees of 90% and 60% (4 h and 8 h demineralization), collagen fibers are exposed with good arrangement, so as to produce more adhesive retention sites for the cells; however, for the bone ECM material with the mineralization degree of 0% (12 h demineralization), the structure of the collagen fibrils is more disordered and the density is worse, which is not conducive to cell retention (as shown in FIG. 2A);

15) observing with an atomic force microscopy (AFM), which also shows that more collagen is exposed on the surfaces of the bone ECM materials with the mineralization degrees of 100%, 90%, 60% and 0% (as shown in FIGS. 3C-3D).

Figure 2B:
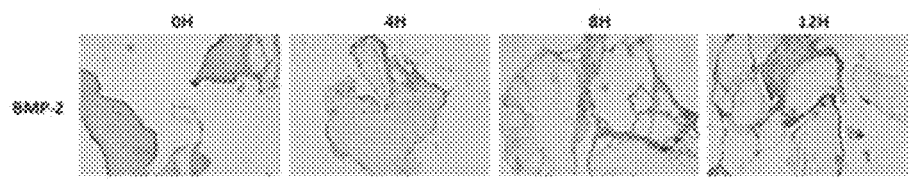
FIG. 2B is immunohistochemical staining images indicating that BMP-2 exposure in the demineralized material is gradually increased.

16) observing with immunohistochemical staining, which shows that BMP-2 expression on the surfaces of the bone ECM materials with the mineralization degrees of 90% and 60% are increased (as shown in FIG. 2B).

Figure 1E:
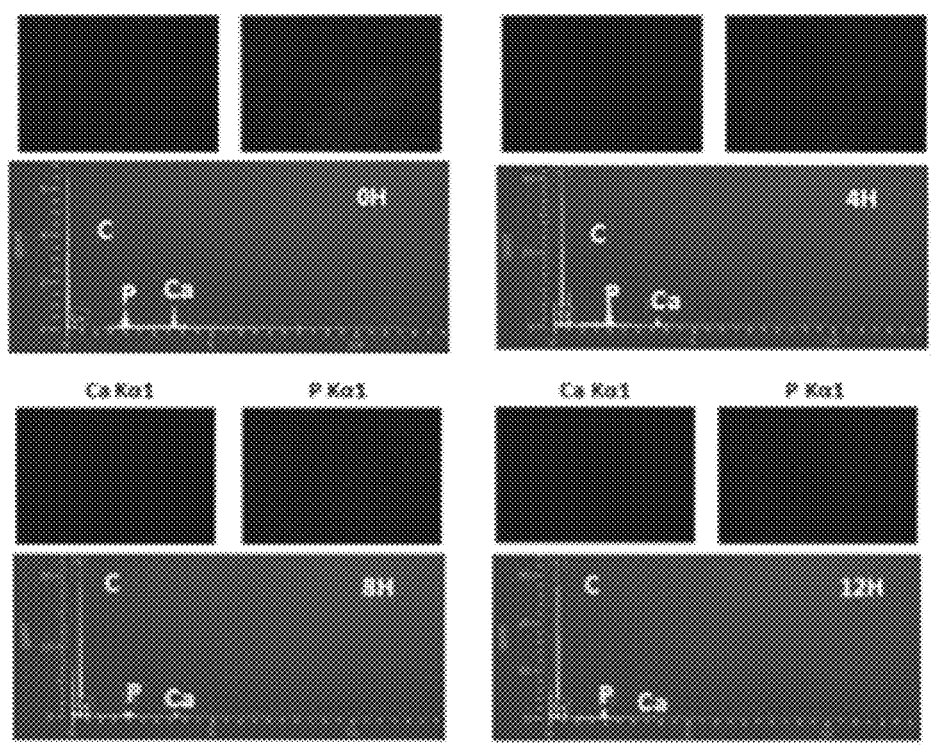
FIG. 1E is EDS analysis diagram indicating that contents of calcium and phosphorus are decreased significantly after the material is demineralized.
Figure 1F:
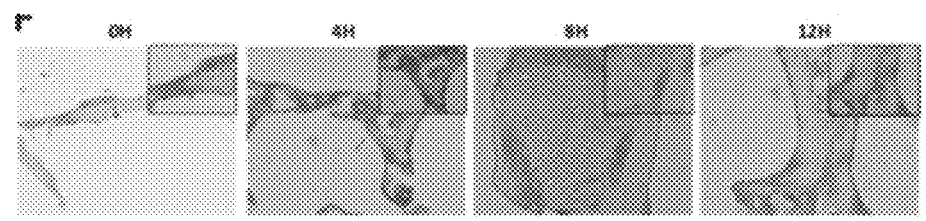
FIG. 1F is Masson dyeing images indicating that exposure of immaturely mineralized collagen fiber is increased after the mineralization degree of the material is reduced, and all groups of cells are completely removed without obvious immunogenic substances after decellularization.

17) detecting ratio of C, P, Ca (carbon, phosphorus, calcium) in specific areas of the bone ECM materials with the mineralization degrees of 100%, 90%, 60% and 0% by an EDS method (as shown in FIGS. 1E-1F); taking C as a reference to measuring Ca concentration according to a selective electrode method, wherein Ca density becomes more dispersed as the mineralization degree decreases; in addition, change in phosphorus content is consistent with change in calcium content, and dispersion degree increases as the mineralization degree decreases; AFM is used to evaluate ultra-microscopic mechanical properties of the mineralization degrees of 100%, 90%, 60% and 0%, wherein with different mineralization degrees of natural bone ECM sources, the bone ECM materials with the mineralization degrees of 90% and 60% have more fibrils exposed on the surfaces, thus providing many RGD ligands for cell adhesion.

Embodiment 4: Transplantation of Bone Marrow Mesenchymal Stem Cells in Bone ECM Material With Mineralization Degrees of 90% and 60%

Figure 4A:
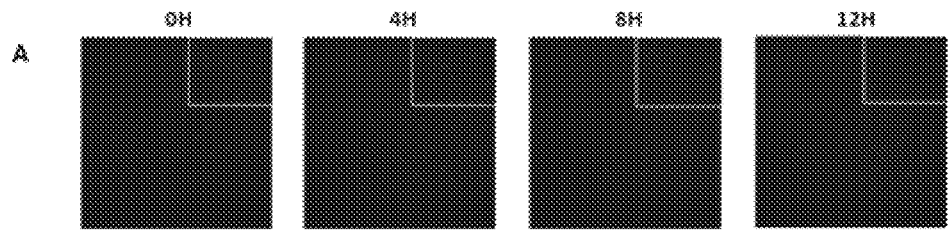
FIG. 4A and FIG. 4B are DAPI staining images and 5000 times magnification electron micrographs indicating cell adhesion ability of the bone ECM materials under the mineralization degrees of 90% and 60%, wherein cell extension is sufficient, but cell adhesion ability of the bone ECM materials under the mineralization degrees of 100% and 0% is poor with insufficient cell extension.
Figure 4B:
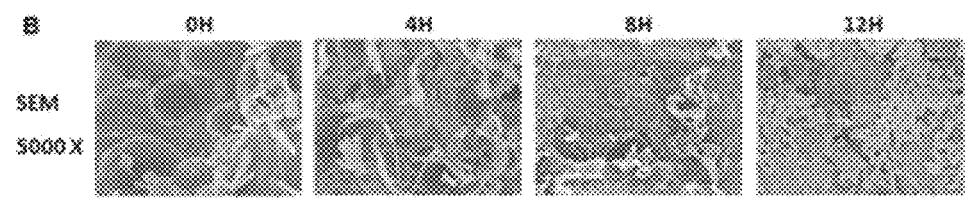
Figure 5A:
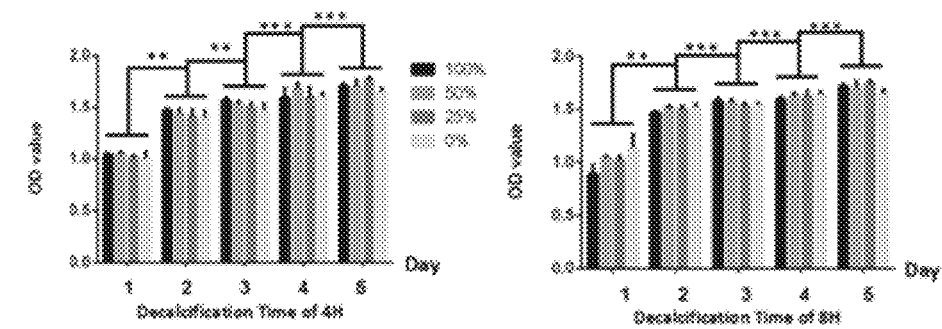
FIG. 5A is histograms indicating that the bone ECM materials with the mineralization degrees of 90% and 60% have no significant effect on proliferation of mesenchymal stem cells after the bone mesenchymal stem cells are cultured in hone ECM material extracts with different concentrations for 1-5 days.
Figure 5B:
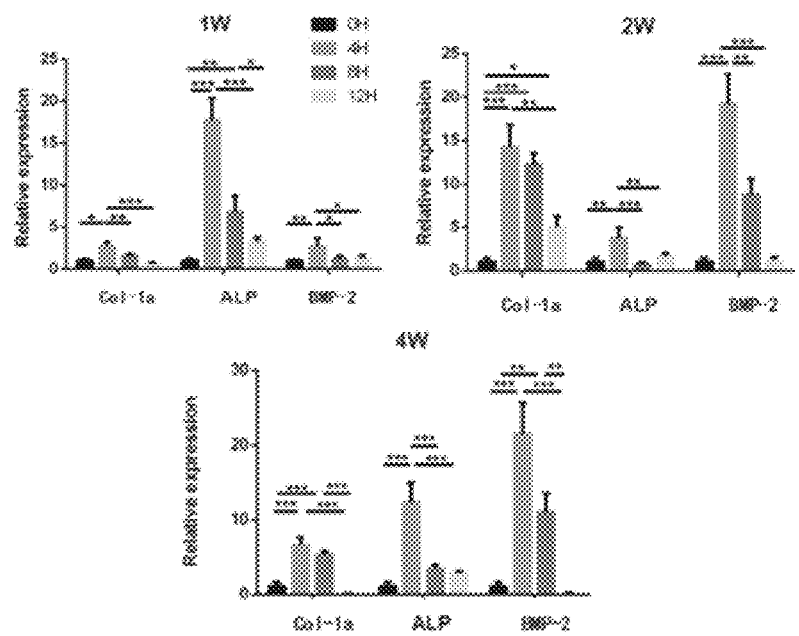
FIG. 5B is histograms indicating relative expression of Col-α, ALP, BMP-2 genes in cells after qPCR detection of re-implantation mesenchymal stein cells of the hone ECM materials with different mineralization degrees, wherein the materials with the mineralization degrees of 90% and 60% have higher expression of osteoinductive proteins.
Figure 6A:
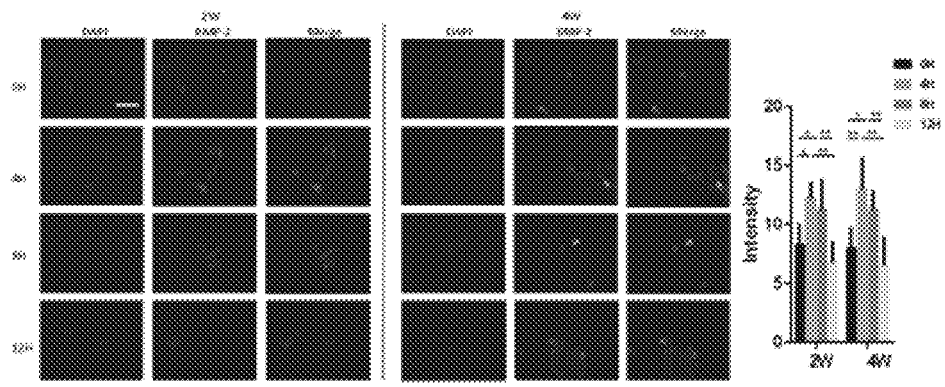
FIG. 6A and FIG. 6B are immunofluorescence staining detection images of relative expression levels of BMP-2 and MEK-1 genes in the mesenchymal stem cells after being implanted into the bone ECM materials with the different mineralization degrees for 2 and 4 weeks, wherein the materials with the mineralization degrees of 90% and 60% have more BMP-2 and MEK-1 expression, suggesting that promotion of BMP-2 expression by the material may be related to stimulation of calcium ions with an appropriate concentration.
Figure 6B:
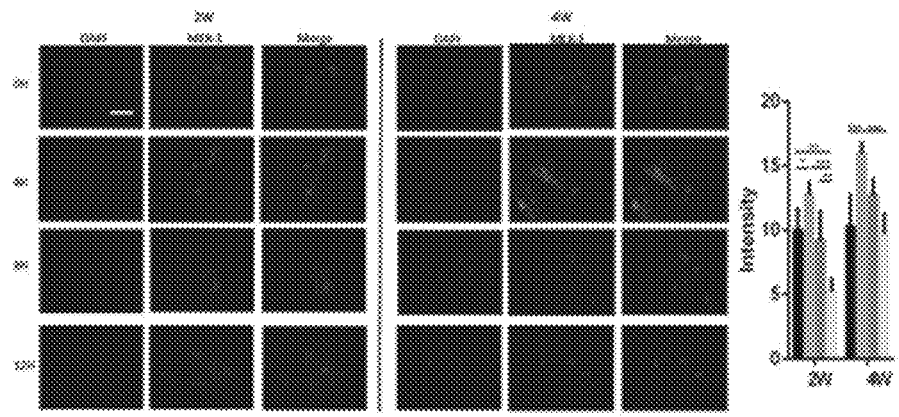

1)-13) are the same as those of the embodiment 1;

14) culturing bone mesenchymal stem cells for 1-5 days with an extract of the bone ECM material with a specific mineralization degree (the extract is derived from the bone ECM materials with the mineralization degrees of 90% and 60%), wherein the cells grows well, indicating that the material is safe and non-toxic (as shown in FIG. 5A);

15) observing after the bone marrow mesenchymal stem cells are transplanted in the bone ECM materials with the mineralization degrees of 100%, 90%, 60% and 0% for 3 days, wherein under confocal microscope observation, the cells are adhered to a scaffold (as shown in FIG. 4A); under 1000 times magnification scanning electron microscope observation, the bone ECM materials with the mineralization degrees of 90% and 60% have more bone marrow mesenchymal stem cells than the bone ECM material with the mineralization degrees of 100%, indicating that the material of the present invention can effectively promote cell adhesion engraftment and proliferation; the bone ECM material with the mineralization degrees of 0% has fewer cells, as shown in FIG. 4B; and 16) comparing relative expression of osteogenic genes in the bone marrow mesenchymal stem cells engrafted on the bone ECM materials with the mineralization degrees of 100%, 90%, 60% and 0% (as shown in FIG. 5B), wherein ALP is one of the most important bone formation indicators of the bone marrow mesenchymal stem cells in an early stage, which shows that the ALP of the cells cultured in the bone ECM material with the mineralization degree of 90% for 1 week is up-regulated by 17 times compared with the non-demineralized group, and Col-1α1 has same trend; At 2nd and 4th weeks of culture, BMP-2 expression of the cells in the bone ECM materials with the mineralization degrees of 90% and 60%, especially the one of 90%, is increased (as shown in FIG. 6A); in addition, a MAPK signaling pathway plays a role in a $Ca^{2+}$-mediated osteogenic differentiation process; compared with the bone ECM materials with the mineralization degrees of 100% and 0%, MEK-1 expression of the cells in the bone ECM materials with the mineralization degrees of 90% and 60% is up-regulated (as shown in FIG. 6B); in summary, the bone ECM materials with the mineralization degrees of 90% and 60%, especially the one of 90%, show better promotion effect on osteogenic differentiation of the bone marrow mesenchymal stem cells than the bone ECM materials with the mineralization degrees of 100% and 0%.

Embodiment 5: Significant Promotion of Early-Stage Bone Defect Repair In Vivo by Bone ECM Materials With Mineralization Degrees of 90% and 60%

Figure 7A:
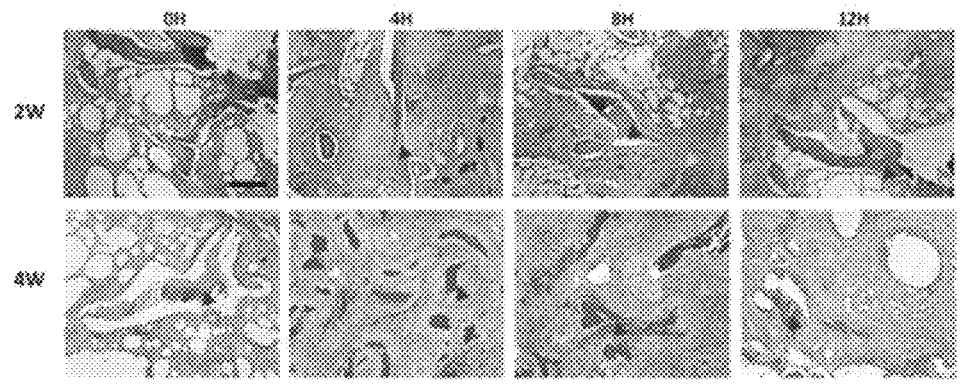
FIG. 7A is Masson three-color staining image of bone defect sites after the bone ECM material is implanted in a rabbit femoral bone defect model for 2 and 4 weeks, indicating that the materials with the mineralization degrees of 90% and 60% have better ability to promote trabecular bone and blood vessel growth.
Figure 7B:
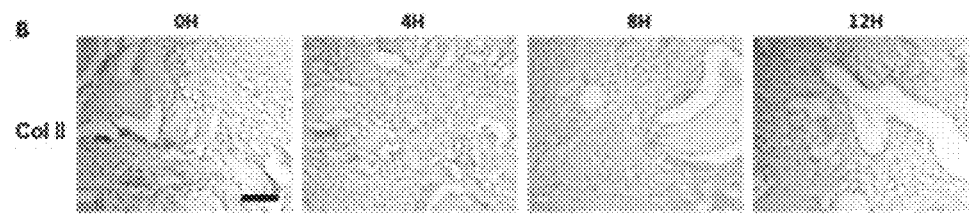
FIG. 7B is immunohistochemical staining images of type II collagen expression in the defect site 2 weeks after implantation, suggesting that the bone ECM material may be involved in an intra-chondral osteogenesis process during promoting bone repair.
Figure 8A:
FIG. 8A is images of angiogenesis in the bone defect site after the bone ECM material is implanted into the bone defect model for 2 weeks, indicating that the materials with the mineralization degrees of 90% and 60% have better angiogenic ability.
Figure 8B:
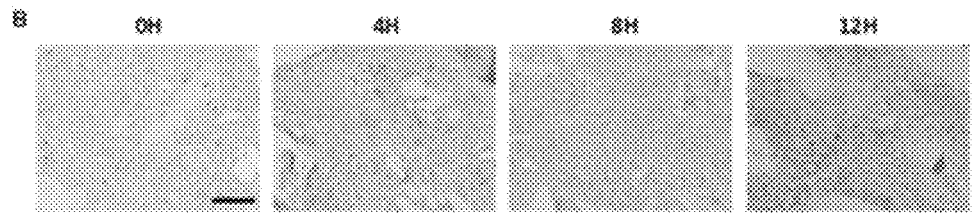
FIG. 8B is images of VEGFA protein expression in the bone defect site after the bone ECM material is implanted into the bone defect model for 2 weeks, indicating that the materials with the mineralization degrees of 90% and 60% can better promote the VEGFA protein expression.
Figure 8C:
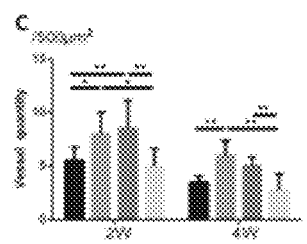
FIG. 8C-8E are quantification histograms of new vessel quantity, area and thickness after the bone ECM material is implanted in the bone defect site for 2 and 4 weeks, indicating that the materials with the mineralization degrees of 90% and 60% have a strong ability to promote blood vessel growth and maturation.
Figure 8D:
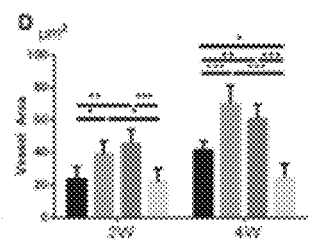
Figure 8E:
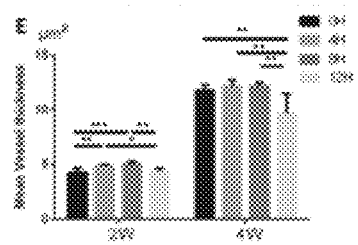
Figure 9A:
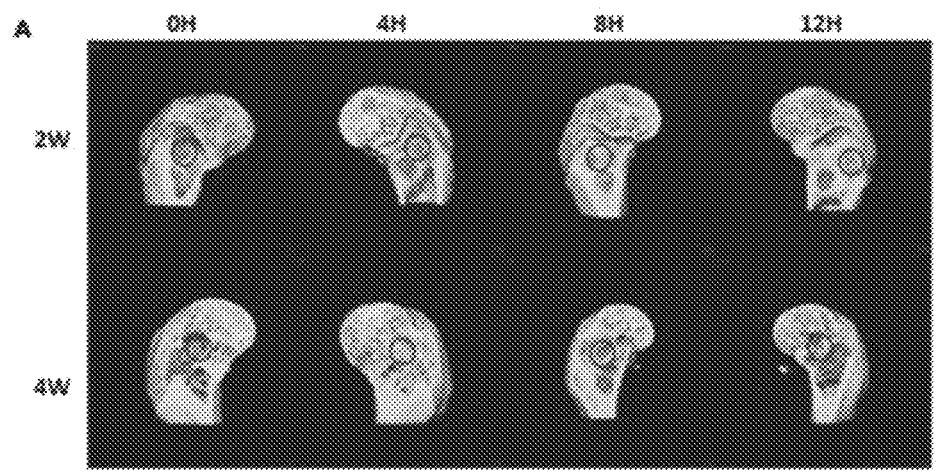
FIG. 9A and FIG. 9B are three-dimensional composite images obtained by MicroCT scanning and reconstruction after the bone ECM material is implanted in the bone defect model for 2 and 4 weeks, wherein the materials with the mineralization degrees of 90% and 60% have batter repair ability the ones of 100% and 0%.
Figure 9B:
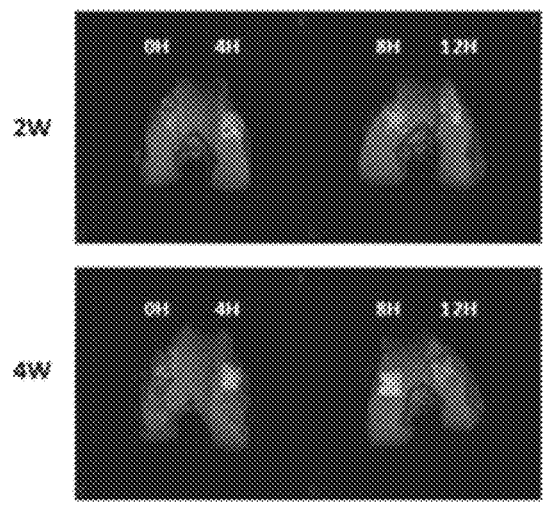
Figure 9C:
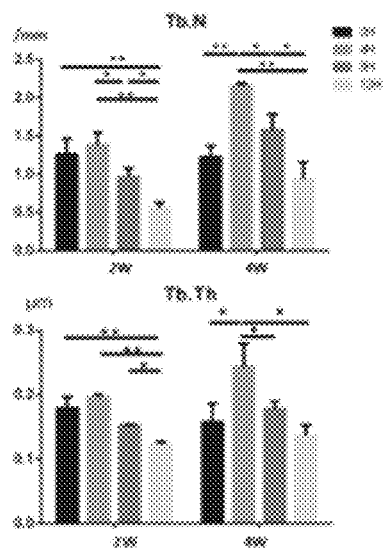
FIG. 9C is histograms of new bone trabeculae quantity and thickness after the bone ECM material is implanted in the bone defect model for 2 and 4 weeks, wherein the materials with the mineralization degrees of 90% and 60% have better ability to promote bone trabecular growth.
Figure 10A:
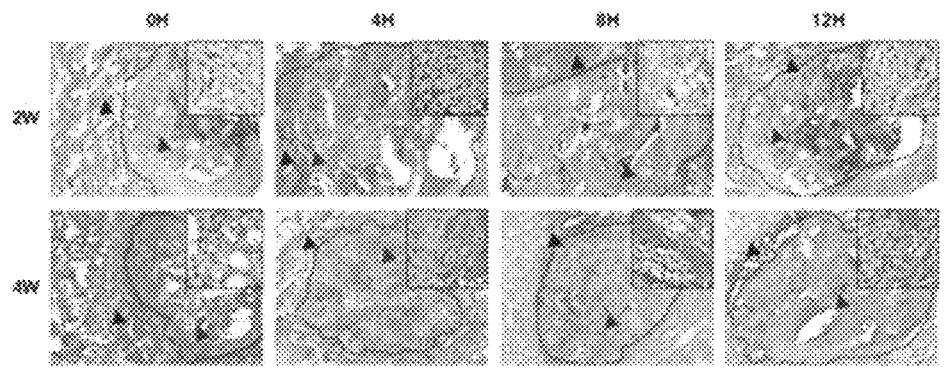
FIG. 10A and FIG. 10B are H&E staining images and repair area quantification histograms after the bone ECM material is implanted in the bone defect model for 2 and 4 weeks, indicating that the bone ECM materials with different mineralization degrees can all promote bone defect repair, while the materials with the mineralization degrees of 90% and 60% have better repair ability than the ones of 100% and 0%.
Figure 10B:
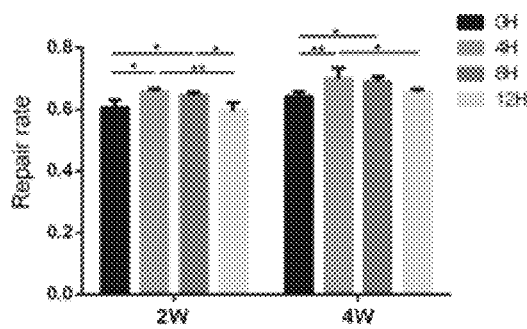

1-3) are the same as those of the embodiment 1;

4) preparing high-temperature sterilized 1 L glass bottles containing 500 ml deionized water and preparing 20 embedding boxes on a sterile operating table with sterile gloves; separating 3 sterilized bone blocks into each embedding box, and putting the embedding box into 10 ml deionized water solution containing 20% acetone and shaking at 10° C. for 4 hours;

5) putting the embedding box into 5 ml deionized water solution containing 1% tributyl phosphate and shaking at 10° C. for 1 hours;

6) putting the embedding box in a deionized water solution containing the protease inhibitor, shaking at 4° C. and 300 rpm for 48 hours with a shaker, and then freezing and thawing with liquid nitrogen for 6 cycles (−80° C./37° C.);

7) putting the embedding box in 5 ml 0.5% Triton® X-100, and shaking with a constant temperature shaker at 10° C. and 100 rpm for 24 hours;

8) shaking the embedding box in deionized water containing 5% SDS with the constant temperature shaker at 10° C. and 100 rpm for 36 h;

9) putting the embedding box in a PBS buffer solution containing 0.5M potassium chloride, and shaking with the shaker at 4° C. and 100 rpm for 2 hours;

10) shaking the embedding box in a PBS buffer containing 1.2M potassium iodide with the shaker at 4° C. and 100 rpm for 12 hours, to obtain decellularized bone ECM materials (as shown in FIG. 1A);

11)-13) are the same as those of the embodiment 1;

14) establishing a rabbit femoral epicondyle bilateral defect model, implanting the bone ECM materials with the mineralization degrees of 100%, 90%, 60% and 0%, and evaluating therapeutic effects;

15) performing Micro-CT analysis (as shown in FIGS. 9A-9B), which shows that after 4 weeks of transplantation, wherein in the bone ECM materials with the mineralization degrees of 90% and 60%, bone detect site are almost filled with new bone trabeculae, while filling effect of the non-demineralized and fully-demineralized material groups is low; the filling effects of the bone ECM materials with the mineralization degrees of 100%, 90%, 60% and 0% are 1.23±0.14/mm, 2.16±0.03/mm, 1.57±0.21/mm and 0.94±0.22/mm, respectively; bone trabecular thicknesses are 0.16±0.03 μm, 0.24±0.04 μm, 0.18±0.01 μm and 0.14±0.02 μm, respectively; growth promotion effects on body new trabecular bone of the bone ECM materials with the mineralization degrees of 90% and 60% are better than the other groups (as shown in FIG. 9C);

16) observing by H&E staining (as shown in FIGS. 10A-10B), which shown no obvious inflammation or inflammatory cells, proving that the material is safety; and 17) observing after 4 weeks of transplantation, wherein the bone ECM materials with the mineralization degrees of 90% and 60% are partially degraded, and new bone has grown into them; collagen fiber mineralization in new bone tissue is mostly surface collagen of immature mineralized materials (as shown in FIGS. 7A-7B).

Embodiment 6: Significant Promotion of Angiogenesis in Bone Defect Parts In Vivo by Bone ECM Materials With Mineralization Degrees of 90% and 60%

1)-4) are the same as those of the embodiment 1;

5) putting the embedding box into 5 ml deionized water solution containing 5% tributyl phosphate and shaking at 10° C. for 4 hours;

6)-7) are the same as those of the embodiment 1;

8) shaking the embedding box in deionized water containing 10% SDS with the constant temperature shaker at 10° C. and 100 rpm for 36 h;

9) putting the embedding box in a PBS buffer solution containing 0.1M potassium chloride, and shaking with the shaker at 4° C. and 100 rpm for 12 hours;

10)-13) are the same as those of the embodiment 1; and 14) observing angiogenesis, wherein new blood vessels are distributed in middle of the trabecular bone; after 2 weeks of transplantation, immature new blood vessels are mostly formed; quantities of new blood vessels of the bone ECM materials with the mineralization degrees of 100%, 90%, 60% and 0% are 5.5±1.3/500 μm$^2$, 8.0±1.6/500 μm$^2$, 8.0±1.8/500 μm$^2$, and 5.0±1.6/500 μm$^2$, respectively; blood vessel areas are 23.92±7.25 μm$^2$, 38.95±8.12 μm$^2$, 45.54±8.70 μm$^2$, and 18.86±9.43 μm$^2$, respectively; new blood vessel thicknesses of the bone ECM materials with the mineralization degrees of 90% and 60% are 4.86±0.15 μm and 5.07±0.20 μm, respectively, which are higher than that of the bone ECM material group with the mineralization degree of 100% (4.29±0.38 μm) and the bone ECM material group with the mineralization degree of 0% (4.41±0.26 μm); after 4 weeks of transplantation, mature new blood vessels are mainly formed; quantities of new blood vessels of the bone ECM materials with the mineralization degrees of 100%, 90%, 60% and 0% are 3.5±0.6/500 μm$^2$; 5.8±1.0/500 μm$^2$, 5.0±0.8/500 μm$^2$, and 2.8±1.5/500 μm$^2$, respectively; the blood vessel areas are 41.26±5.69 μm$^2$; 69.92±11.26 μm$^2$, 60.76±8.66 μm$^2$, and 24.87±8.18 μm$^2$, respectively; thicknesses are increased in each group compared with those after 2 weeks of transplantation, wherein the bone ECM material group with the mineralization degree of 90% (12.18±0.54 μm) and the bone ECM material group with the mineralization degree of 60% (12.18±0.32 μm) are still higher than that of the bone ECM material group with the mineralization degree of 100% (11.83±0.49 μm) and the bone ECM material group with the mineralization degree of 0% (9.68±1.83 μm), the bone ECM material groups with the mineralization degrees of 90% and 60% have promoted growth of new blood vessels, microvessel degeneration, and stable growth of large blood vessels compared with the other two groups, and distribution of vascular endothelial growth factor A (VEGFA) in detect tissue is up-regulated, so as to provided better repair effect (as shown in FIGS. 8A-8E).

Embodiment 7: Research and Evaluation of Gradient Mineralized Cancellous Bone Matrix Material and Preparation Method Thereof 1) selecting fresh bovine scapula and washing for 4 times with sterile saline, removing cancellous bone with a 6 mm drill, and cutting the cancellous bone into cylindrical bone blocks about 2 mm high with a scalpel;

2) then rinsing the bone blocks with sterile physiological saline for 2 hours before sending to an irradiation center for sterilizing by irradiation, wherein an irradiation dose is 25 w;

3) rinsing the bone blocks with deionized water containing 50 KIU/ml protease inhibitor for 2 times and 5 minutes for each time, to remove blood, fat tissue and other impurities; and 4) performing subsequent operations with reference to the method of the embodiment 1, to obtain the gradient mineralized cancellous bone matrix material.

Embodiment 8: Research and Evaluation of Gradient Mineralized Cancellous Bone Matrix Material and Preparation Method Thereof 1) selecting fresh porcine rib and washing for 4 times with sterile saline, removing cancellous bone with a 6 mm drill, and cutting the cancellous bone into cylindrical bone blocks about 2 mm high with a scalpel;

2) then rinsing the bone, blocks with sterile physiological saline for 2 hours before sending to an irradiation center for sterilizing by irradiation, wherein an irradiation dose is 25 w;

3) rinsing the bone blocks with deionized water containing 10 KIU/ml protease inhibitor for 5 times and 5 minutes for each time, to remove blood, fat tissue and other impurities; and 4) performing subsequent operations with reference to the method of the embodiment 1, to obtain the gradient mineralized cancellous bone matrix material.

Embodiment 9: Research and Evaluation of Gradient Mineralized Cancellous Bone Matrix Material and Preparation Method Thereof 1)-3) are the same as those of the embodiment 1;

4) preparing high-temperature sterilized 1 L glass bottles containing 500 ml deionized water and preparing 20 embedding boxes on a sterile operating table with sterile gloves; separating 3 sterilized bone blocks into each embedding box, and putting the embedding box into 10 ml deionized water solution containing 10% acetone and shaking at 10° C. for 1 hour;

5) putting the embedding box into 5 ml deionized water solution containing 2% tributyl phosphate and shaking at 10° C. for 4 hours;

6) putting the embedding box in a deionized water solution containing the protease inhibitor, shaking at 4° C. for 24 hours with a shaker, and then freezing and thawing with liquid nitrogen for 3 cycles (−80° C./37° C.);

7) putting the embedding box in 5 ml 2% Triton® X-100, and shaking with a constant temperature shaker at 10° C. and 100 rpm for 24 hours;

8) shaking the embedding box in deionized water containing 5% SDS with the constant temperature shaker at 10° C. and 100 rpm for 36 h;

9) putting the embedding box in a PBS buffer solution containing 0.5M potassium chloride, and shaking with the shaker at 4° C. and 100 rpm for 6 hours;

10) shaking the embedding box in a PBS buffer containing 1M potassium iodide with the shaker at 4° C. and 100 rpm for 6 hours, to obtain decellularized bone ECM materials (as shown in FIG. 1A);

11) preparing a decalcification solution (deionized water 1750 ml+EDTA−2Na 450 g+NaOH 10 g); taking out the bone blocks and decalcifying in an ultrasound decalcifier at 350 kHz and 4° C. for 4, 8, 12 and 24 h; and 12) performing subsequent operations with reference to the method of the embodiment 1, to obtain the gradient mineralized cancellous bone matrix material.

The gradient mineralized cancellous bone matrix materials obtained in the embodiments 7-9 are subjected to histological evaluation, calcium and phosphorus content detection, collagen surface morphology and content detection, and mechanical detection. The results are the same as those in the embodiment 1, which indicates that the gradient mineralized cancellous bone matrix materials with similar effects can be prepared by the above optimized reagents and adjusted processing time. In addition, the histological evaluation, cell culture experiments, and in-vivo repair experimental evaluation and test of the materials all indicate that the gradient mineralized cancellous bone matrix materials with mineralization degrees of 90% and 60% obtained in the embodiments 7-9 have good repair and regeneration effects. The materials can be used as a safe, reliable, effective and fast biomaterial for clinically promoting repair and regeneration of muscle defect and lesion.

What is claimed is:

1. A preparation method of a gradient mineralized cancellous bone matrix material, the method comprising the steps of: step 1: randomly selecting bone tissue from a mammal, removing the bone tissue with a drill, and cutting the bone tissue into cylindrical bone blocks with a scalpel; step 2: rinsing the bone blocks with sterile physiological saline for 2 hours before sterilizing by irradiation, wherein an irradiation dose is 5-40w; step 3: rinsing the bone blocks with deionized water containing a protease inhibitor to remove blood, fat tissue and other impurities, wherein a concentration of the protease inhibitor in the deionized water is 10-50 KIU/mL, and the bone blocks are rinsed with the deionized water for 2-6 times and 3-20 minutes for each time; step 4: separating the bone blocks into an embedding box, and putting the embedding box into a deionized water solution containing acetone and shaking for 1-4 hours, wherein a volume ratio of the acetone to deionized water in the deionized water solution is 10-20%; step 5: putting the embedding box into a deionized water solution containing tributyl phosphate and shaking for 1-4 hours, wherein a volume ratio of the tributyl phosphate to deionized water in the deionized water solution is 1-5%; step 6: putting the embedding box in a deionized water solution containing the protease inhibitor, shaking at 4° C. for 24-48 hours with a shaker, and freezing with liquid nitrogen, and thawing, for 2-6 cycles, wherein each cycle is from −80° C. to 37° C., and a shaker speed is 50-300 rpm; step 7: putting the embedding box in a buffer solution containing polyethylene glycol mono(4-tert-octyl phenyl) ether, and shaking with a constant temperature shaker for 24 hours, wherein a concentration of the polyethylene glycol mono(4-tert-octyl phenyl) ether is 0.5-5% vol; step 8: shaking the embedding box in a buffer solution containing sodium dodecyl sulfate (SDS) with the constant temperature shaker for 36 hours, wherein a concentration of the SDS is 0.5-10% vol; step 9: putting the embedding box in a phosphate buffer solution (PBS) having a concentration of potassium chloride of 0.1-1M, and shaking with the shaker at 4° C. and 100 rpm for 2-12 hours; step 10: shaking the embedding box in a PBS buffer containing potassium iodide with the shaker, at a temperature of 4° C., and 100 rpm for 2-12 hours, wherein a concentration of the potassium iodide in deionized water is 1-1.5M; step 11: performing the ultrasound gradient demineralization treatment in a NaOH buffer solution containing EDTANa$_2$ at 4°

C.-10° C. for 4, or 8, or 12, or 24 hours, so as to obtain bone Extracellular Matrix (ECM) materials with mineralization degrees of 100%, or 90%, or 60%, or 0%; and step 12: sterilizing the obtained materials by irradiation; wherein after each of the steps 4-11, the deionized water is used to rinse for 6 hours before a next step.

2. The preparation method, as recited in claim 1, wherein in the deionized water containing the protease inhibitor, the concentration of the protease inhibitor is 20-40 KIU.

3. The preparation method, as recited in claim 1, wherein in the deionized water solution containing the acetone, the volume ratio of the acetone to the deionized water is 13%-18% vol.

4. The preparation method, as recited in claim 1, wherein in the deionized water solution containing the tributyl phosphate, the volume ratio of the tributyl phosphate to the deionized water is 2%-5% vol.

5. The preparation method, as recited in claim 1, wherein the shaker speed is 30-180 rpm.

6. The preparation method, as recited in claim 1, wherein the concentration of the polyethylene glycol mono(4-tert-octyl phenyl) ether is 0.5-3% vol.

7. The preparation method, as recited in claim 1, wherein the concentration of the SDS is 0.5-5% vol.

8. The preparation method, as recited in claim 1, wherein the concentration of the potassium chloride in deionized water is 0.3-1M.

9. The preparation method, as recited in claim 1, wherein the concentration of the potassium iodide in the deionized water is 1-1.4M.

* * * * *